United States Patent
Choi

(10) Patent No.: US 6,191,342 B1
(45) Date of Patent: Feb. 20, 2001

(54) TRANSGENIC MICE EXPRESSING THE HIK-RAS 4B CHIMERIC GENE

(75) Inventor: Tae Saeng Choi, Taejon-si (KR)

(73) Assignee: LG Chemical Ltd., Seoul (KR)

( * ) Notice: Under 35 U.S.C. 154(b), the term of this patent shall be extended for 0 days.

(21) Appl. No.: 09/355,070

(22) PCT Filed: Dec. 2, 1998

(86) PCT No.: PCT/KR98/00396

§ 371 Date: Jul. 22, 1999

§ 102(e) Date: Jul. 22, 1999

(87) PCT Pub. No.: WO99/29846

PCT Pub. Date: Jun. 17, 1999

(51) Int. Cl.[7] .................. A01K 67/00; A01K 67/033; C12N 15/00; C12N 1/20; C07H 21/04
(52) U.S. Cl. .................. 800/10; 800/10; 800/18; 800/25; 435/252.33; 435/471; 435/476; 435/320.1; 536/23.1; 536/23.5
(58) Field of Search .................. 800/8, 9, 10, 18, 800/24, 25; 435/320.1, 252.33, 471, 476; 536/23.1, 23.5

(56) References Cited

PUBLICATIONS

Barrington, R.E. et al. A Farnesyltransferase Inhibitor Induces Tumor Regression in Transgenic Mice Harboring Multiple Oncogenic Mutations by Mediating Alterations in Both Cell Cycle Control and Apoptosis. Molecular and Cellular Biology 18(1):85–92, Jan. 1998.*

Tremblay, P.J. et al. Transgenic Mice Carrying the Mouse Mammary Tumor Virus Fusion Gene: Distinct Effects in Various Tissues. Molecular and Cellular Biology 9(2):854–859, Feb. 1989.*

Mangues, R. et al. An Overexpressed N–ras Proto–Oncogene Cooperates with N–Methylnitrosurea in Mouse Mammary Carcinogenesis. Cancer Research 54:6395–6401, Dec. 1994.*

Hirohashi, A. et al. Monoclonal Antibody. Patent Abstracts of Japan 13(293): JP1086882, Jul. 1989.*

Kappel, C.A. et al. Regulating gene expressionin transgenic animals. Current Opinion in Biotechnology 3:548–553, 1992.*

Wall., Transgenic Livestock: Progress and Prospects for the future, Theriogenology 45:57–68, (1996) pp. 57–68.*

E. Sinn et al. "Coexpression of MMTV/v–Ha–ras and MMTV/c–myc Genes in Transgenic Mice: Synergistic Action of Oncogenes in Vivo", Cell, vol. 49, No. 4, May 22, 1987, pp. 465–475.

R. Mangues et al., "Tumorgenesis and male sterility in transgenic mice expressing a MMTV/N–ras oncogene", Oncogene, vol. 5, 1990, pp. 1491–1497.

* cited by examiner

*Primary Examiner*—Deborah J. R. Clark
*Assistant Examiner*—Eleanor Sorbello
(74) *Attorney, Agent, or Firm*—Bachman & LaPointe, P.C.

(57) ABSTRACT

A transgenic mouse whose genome comprises the H/K-ras 4B chimeric gene to form a mammary tumor and, particularly, the expression vector producing H/K-Ras 4B chimeric protein by using MMTV (mouse mammary tumor virus) promoter. This protein contains the first 164 amino acids of the H-Ras followed by the last 24 amino acids of K-Ras 4B. The second, it relates to the transgenic mouse expressing the H/K-Ras 4B protein with a mammary tumor, and the third, the method of preparation.

7 Claims, 3 Drawing Sheets

TRANSGENIC MICE EXPRESSING THE H/K-RAS 4B CHIMERIC GENE

CLAIM FOR PRIORITY

The instant application claims the benefit of priority for PCT/LR98/00396.

FIELD OF THE INVENTION

The present invention relates to the transgenic mouse expressing the H/K-ras 4B chimeric gene to form a mammary tumor. Particularly, the present invention relates to the expression vector producing H/K-Ras 4B chimeric protein by using MMTV (mouse mammary tumor virus) promoter. This protein contains the first 164 amino acids of the H-Ras with valine in place of glycine of the 12th amino acid residue followed by the last 24 amino acids of K-Ras 4B. Secondly, it relates to the transgenic mouse expressing the H/K-Ras 4B protein with a mammary tumor, and the third, the method of preparation thereof. Transgenic mouse of the 15 present invention can be used as a useful tool not only to research a function of ras-oncogene but also to screen in vivo efficacy anti-cancer drug, especially which targeted ras-blocker.

BACKGROUND OF THE INVENTION

Ras protein is 21 kDa GTP-binding protein containing GTPase activity, and involved in cell growth and differention. Cycling of active Ras, GTP-bound forms is accomplished by the proteins' intrinsic GTPase activity and a number of accessory preteins (Bourin, H. R., Sanders, D. A., McCormick, F., Nature, 349, 117, 1991). The mammalian ras gene family contains three homologous members, H-ras, K-ras and N-ras. K-ras gene produces two different proteins K-Ras 4A and K-Ras 4B being splice variants of the same gene. Each ras-gene encodes a 21-kDa protein of either 188 (K-Ras 4B) or 189 (H-Ras, K-Ras 4A and N-Ras) amino acids residues. All three ras oncogene differ from the wild type by a single amino acid change at residue 12, 13, or 61 due to point mutation in the ras proto-oncogenes. Three mutations inhibit inherent GTPase activity of Ras protein, consequently maintained active state of Ras, GTP-binding form which produce abnormal growth signal.

It has been reported that the abnormalities of the signal transduction induces carcinogenesis. Practically oncogenic ras gene associated with these mutations has been known to be related to 30–40% of human cancers such as pancreas cancer, bladder cancer, lung cancer, skin cancer and the like. Nowadays, new attempts have been proceeded to develop anticancer agents targeted oncogenic-ras gene to inhibit carcinogenesis (Bos, J. L., Cancer Res., 49, 4682, 1989).

As described above, mammalian cells have 4 types of Ras proteins, which have very similar structure. In particular, the amino acid sequences of Ras protein are the same completely at the N-terminus from amino acid residue 1 to 86 and almost the same in ratio of 90% from amino acid residues 87 to 164. However, the amino acid sequences are very different at the C-terminus from amino acid residues 165 to end. Especially, K-Ras proteins have specific amino acid residues, lysine rich domain at the C-terminus, which discriminates K-Ras protein from N-Ras or H-Ras proteins.

Ras protein should be attached onto plasma membrane in order to show biological activities. Therefore, Ras protein should be processed for post traslational modifications by using various enzymes before it attaches onto plasma membrane. The first, the modification is catalysed by the enzyme farnesyltransferase. The enzyme covalently links a farnesyl group (a 15-carbon isoprenoid) to a cystein residue located in the carboxyl terminal $CA_1A_2X$ motif of Ras (in which C is cystein, $A_1$ and $A_2$ are aliphatic amino acid, and X is methionine or serine). This is followed by hydrolysis of the $A_1A_2X$ sequence, metylation of the terminal carboxylate group and palmitoylation of the upstream several cystein residues.

Said farnesylation is induced at the cystein residue so as to form sulfide-ether bonding. Especially, in H-Ras and N-Ras protein, palmitoylation also occurs at the other cystein residues adjacent to the C-terminus. As a result of the farnesylation, Ras protein becomes hydrophobic and can attach onto plasma membrane. The farnesyl group of Ras protein has been known to bind easily with lipid bilayer of plasma membrane.

Although all steps of the modification described above are needed in order that Ras protein attaches suitably onto cell membrane, it also has been reported that the farnesylation is enough to show inherent Ras transforming activity. Therefore, farnesyl transferase inhibitor were developed as potential anticancer agents that would block farnesylation and thus inhibit the function of oncogenic Ras (Buss, J. E. et al., Chemistry & Biology, 2, 787, 1995).

Recently, a new animal model has been developed to evaluate anticancer agents useful clinically. As a result, transgenic animals which include activated oncogene such as ras or lack tumor suppressor gene, p53 have been obtained. In particular, Leder has reported to produce transgenic animal expressing v-H-Ras protein from the MMTV (mouse mammary tumor virus) promoter (Leder, P. et al., Cell, 49, 465, 1987). Gordon has produced transgenic animal expressing N-Ras protein from the MMTV promoter (Gordon, J. W., Oncogene, 5, 1491, 1990). However, transgenic animal using activated K-Ras gene has not yet been developed.

In the meantime, the inhibition effect of FTase inhibitor on the farnesylation of Ras proteins in vitro has been estimated. It has been found that the substrate specificity of the inhibitors are different according to the amino acid sequences of the C-termini in H-Ras protein, N-Ras protein and K-Ras protein respectively. Recent reports have shown that K-Ras, whose C-terminus CVIM predicts farnesylation, can also be geranylgeranylated in vitro, and that its prenylation in cells is inhibited by a GGTaseI inhibitor. Since the mutation in K-Ras 4B are by far the most frequent in human tumors, transgenic mouse expressing K-ras oncogene actively needs to be used for evaluation in vivo efficacy of FTase inhibitors.

In order to obtain transgenic mice with mammary tumors which can be utilized in estimating inhibition effects on farnesyl transferase activity in vitro, the present invention has constructed the expression vector containing H/K-ras 4B chimeric gene and producing the chimeric fused protein at the mouse mammary gland. Then the expression vector has been microinjected into mouse one-cell embryos and the eggs have been transfered into recipient mice to produce transgenic mice. And in order to identify the incorporation of H/K-ras 4B gene into genomic DNA sequence, polymerase chain reaction (PCR) and Southern blot were accomplished finally. Additionally, the expression of H/K-ras 4B genes was confirmed by RT-PCR and Northern blot in specific tissues.

SUMMARY OF THE INVENTION

The object of the present invention is to provide a transgenic mouse expressing carcinogenic gene with mammary tumor and a process for preparation thereof.

The present invention provides the transgenic mouse which contains H/K-ras 4B gene in cells and have mammary tumor. The transgenic mouse expresses H/K-ras 4B gene containing the C-terminal sequences of K-ras 4B gene.

The present invention provides the expression vector which can express H/K-ras 4B gene in mouse mammary glands.

Particularly, the expression vector pMAM neo genomic H-Ras-K-ras 4B expressing genomic H/K-ras 4B gene from the mouse mammary tumor virus (MMTV) promoter is provided.

E. Coli MC1061 strain was transformed by the expression vector pMAM neo genomic H-Ras-K-Ras 4B and the transformant has been deposited with Korea Research Institute of Bioscience and Biotechnology, Daejon, Korea, on Dec. 2, 1997 (accession number: KCTC 0411 BP).

The present invention provides a process for preparing the transgenic mouse which comprises;

(1) microinjecting H/K-ras 4B gene into a fertilized egg, and (2) transfering the fertilized egg onto a mouse oviduct.

Figure 3:
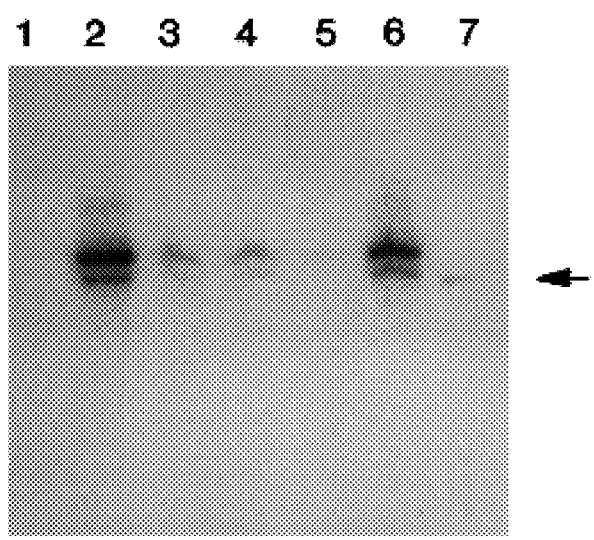
Figure 4:
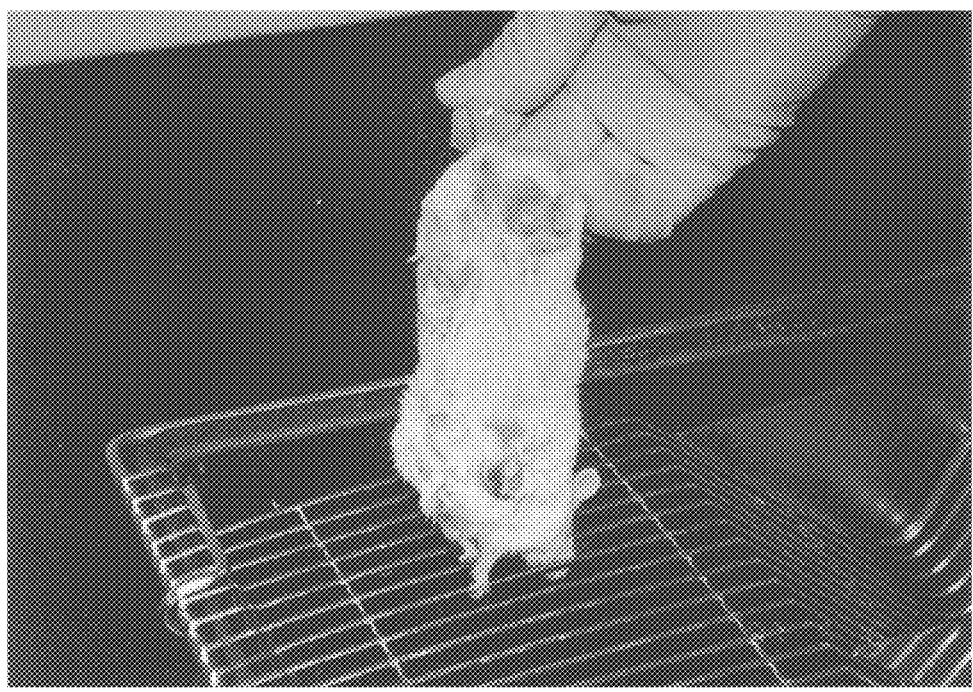

lane 1: wild-type mice;

lane 2–6: transgenic mice;

lane 7: expression vector pMANI neo genomic H/K-Ras 4B$^{V12}$;

FIG. 3 depicts the genomic fragment of the H/K-ras 4B$^{V12}$ gene inserted into transgenic mice by performing Southern Blot.

lane 1: wild-type mice;

lane 2–5: transgenic mice:

lane 6: the expression vector pMAM neo genomic H-Ras-K-Ras 4B;

FIG. 4 depicts the photograph of the transgenic mouse of the present invention.

DETAILED DESCRIPTION OF THE INVENTION

The present invention provides transgenic mice whose cells carry H/K-ras 4B gene containing valine in place of glycine of the 12th amino acid residue and have a mammary tumor.

This invention exploits the gene coding fusion protein (H/K-Ras 4B) which has been produced by ligating the N-terminal concensus sequence originated from H-Ras, amino acid residues 1 to 164, and C-terminal unique sequence originated from K-Ras 4B, amino acid residues 165 to 188. At that time oncogenic H-Ras protein contains Val in place of Gly as the 12th amino acid residue.

The said gene is injected into the male pronucleus of mouse one-cell embryo.

In addition, this invention provides the expression vector which can express H/K-ras 4B gene at the mammary glands of a mouse.

Particularly, in order to obtain said fusion gene, H-Ras gene has been separated from the expression vector pHO6T1 by carrying out polymerase chain reaction (PCR) which utilized primers of SEQ ID. NO: 1 and SEQ ID. NO:2. K-ras 4B gene has been obtained by digesting the expression vector pCDNA H-Ras-K-Ras 4B with the restriction enzyme Eco RI and Xho I. and two elements obtained as above have been ligated.

The expression vector pMAM neo genomic H-Ras-K-Ras 4B of this invention has been constructed by inserting the fusion gene prepared as above into the plasmid vector pMAM neo which contains MMTV promoter.

E. coli MC1061 strain was transformed by the expression vector pMAM neo genomic H-Ras-K-Ras 4B and the transformant has been deposited with Korea Research Institute of Bioscience and Biotechnology (KRIBB), Korea Institute of Science and Technology (KIST), Taejon, Korea, on Dec. 2, 1997 (accession number: KCTC 0411 BP).

In addition, this invention provides the process for preparation of a transgenic mouse by microinjection into the fertilized egg of a mouse using the said expression vector pMAM neo genomic H-Ras-K-Ras 4B.

In details, the fertilized eggs have been obtained by driving over-six week old females which were selected among FVB/N inbred mice to superovulate. The fusion gene above has been microinjected into the male pronuclei of fertilized ova. At that time, it is preferable that the fertilized eggs in one-cell stage are utilized.

The injected mouse eggs have been cultured in modified Whittin's medium (mWM) and the next day, 2-cell embryos were selected and transferred into the oviduct of recipient females.

Figure 1:
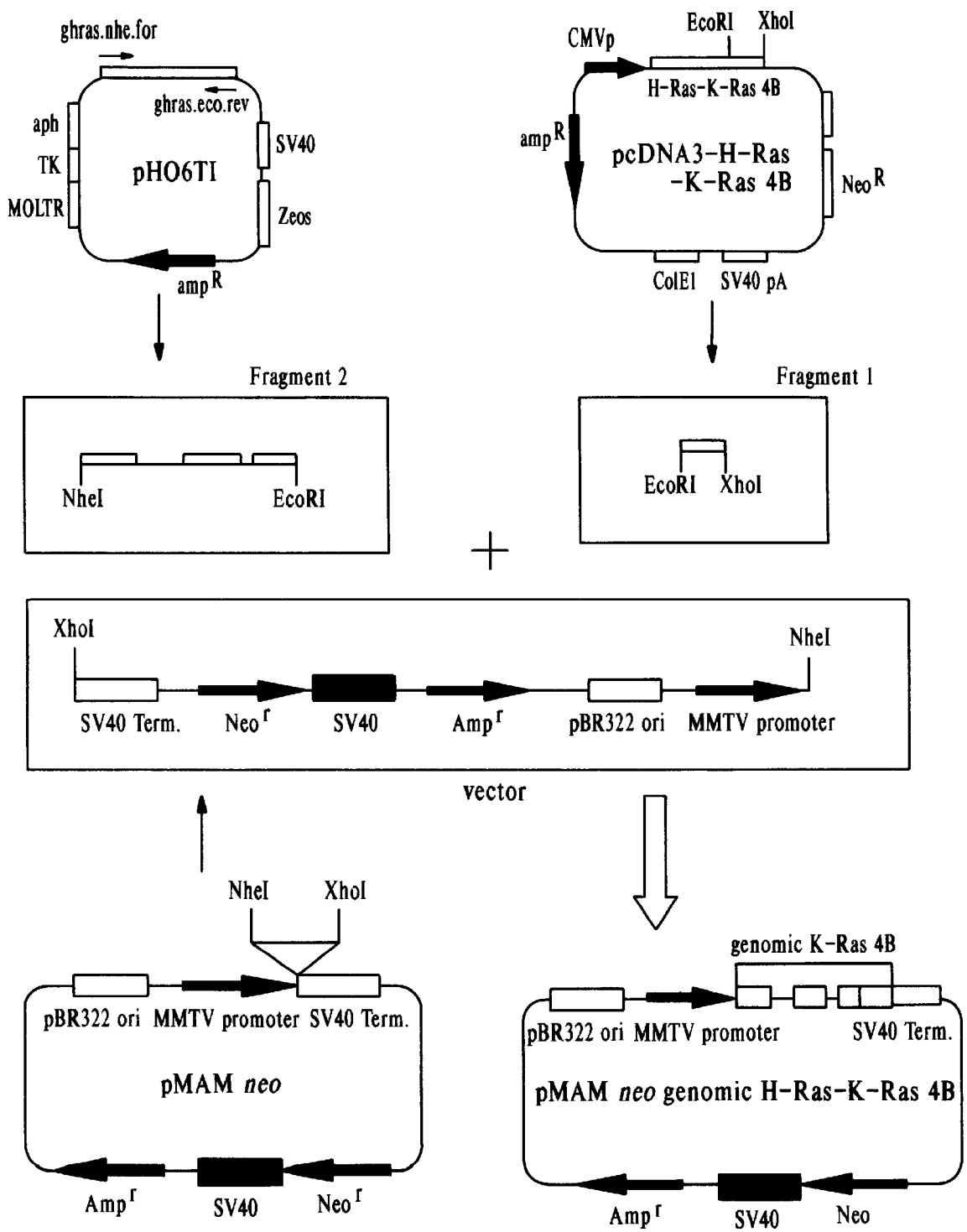
FIG. 1 depicts a strategy for the construction of the expression vector containing human H/K-ras 4B gene under the control of MMTV promoter.
Figure 2:
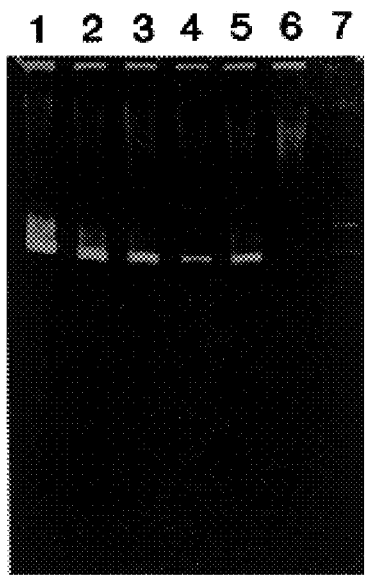
FIG. 2 depicts the PCR analysis of H/K-ras 4B gene in genomic DNA sequences to detect transgenic mice.

In order to examine the gene of transgenic mice prepared as above, chromosomal DNA has been obtained from the tail of mice and analyzed by carrying out PCR. As a result five clones have been proved to be transgenic mice carrying H/K-ras 4B gene (see FIG. 1) and H/K-ras 4B gene has been identified by performing Southern blot (see FIG. 2).

Transgenic mice of the present invention contain H/K-ras 4B gene in their germ and somatic cells, and exhibit the pathology associated with mammary tumors over-expressing H/K-ras 4B gene in mammary glands.

Since the amino acid sequence of the C-terminus originated from K-Ras 4B protein is an important element for farnesylation, transgenic mice above carrying H/K-ras 4B gene with mammary tumors can be used efficiently to evaluate the compounds which inhibit farnesyl transferase. Furthermore the said transgenic mice can be used fitly to examine oncogenic mechanism related with the abnormality of Ras signal transduction system.

Practical and presently preferred embodiment of the present invention is illustrative as shown in the following Examples.

However, it will be appreciated that those skilled in the art, on consideration of this disclosure, may make modification and improvements within the spirit and scope of the present invention.

EXAMPLES

Example 1

Cloning of K-ras 4B Gene and H-ras Gene

In order to obtain K-ras 4B gene, 1 μg of the expression vector pCDNA H-Ras-K-Ras 4B (KR patent application No. 97-14409) was dissolved in distilled water (D.W.) 85 μl and 10× reaction buffer 10 μl, restriction enzyme EcoR I , Xho I 2.5 μl respectively were added. Then the reaction mixture was incubated at 37° C. for 2 hours. As a result, 155bp DNA fragment was separated by polyacrylamide gel electrophoresis (fragment 1) and dissolved in 20 μl of D.W.

H-ras gene was obtained from the expression vector pHO6T1 (D. A. Spandidos and N. M. Wilkie, Nature, Vol. 310) by performing PCR which utilized oligonucleotides of SEQ ID. NO:1(ghras. nhe. for) and SEQ ID. NO:2(ghras. eco. rev) as forward primer and reverse primer respectively. In details, 10 ng of the expression vector pHO6T 1 and 1 µl of each primer (0.27 µg/µl ) above were added to the tube containing 10× reaction buffer (Promega, USA) 10 µl, 25mM MgCl$_2$ 6µl, 1mM dNTP 1 µl, Taq polymerase 1 unit (Promega, USA) and DMSO 10 µl. Then the reaction mixture were adjusted to be 100 µl with D. W. And 859 bp fragment of H-Ras DNA was separated by performing PCR for 30 cycles (94° C. 80 sec., 52° C. 105 sec., 72° C. 150 sec.) using the reaction mixture above and analyzed by polyacrylamide gel electrophoresis. This fragment was mixed with 10 µl of 10× reaction buffer, 2.5 µl of restriction enzyme Nhe I, EcoR I respectively and the reaction mixture was adjusted to be 100 µl with D. W., then reacted at 37° C. for 20 hours. The fragment prepared as above was separated by polyacrylamide gel electrophoresis and dissolved in 20 µl of D. W.

The expression vector pMAM neo (clontech, USA) which contains MMTV promoter was digested with restriction enzyme Nhe I and Xho I and transfered to the tube containing 3 µl of fragment 1, 8 µl of fragment 2, 10 µl of 10× reaction buffer and 1 unit of T4 DNA ligase (Beoringer Mannheim, Germany). The reaction mixture was adjusted to be 15 µl and reacted at 16° C. for 16 hours.

The *E. coli* clones obtained as previous process were analyzed and finally the expression vector pMAM neo genomic H-Ras-K-Ras 4B of this invention was constructed.

Example 2
Separation of H/K-ras 4B Gene for Microinjection

In order to microinject the gene, about 4kb gene fragment which contains promoter, H/K-ras 4B gene and polyadenylation signal was separated by digesting with restriction enzyme from the expression vector pMAM neo genomic H-Ras-K-Ras 4B.

In a preferred embodiment, the expression vector pMAM neo genomic H-Ras-K-Ras 4B was added to the tube containing 10× reaction buffer 10 µl, restriction enzyme HindIII 5 µl and the reaction mixture was adjusted to be 100 µl, then reacted at 37° C. for 2 hours so as to separate about 4kb fragment by performing agarose gel electrophoresis.

Example 3
Microinjection of H/K-ras 4B Gene

The fertilized eggs were obtained by driving over-six week old donor females which were selected among FVB inbred mice (Charles riber Co.) to superovulate.

It is preferable that the fertilized eggs in one-cell stage are utilized. The adequate time for microinjection is controlled according to the light-dark cycle of the mouse-breeding farm, particularly in the present invention the light was turn on at 6:00 a.m. and off at 6:00 p.m. and the microinjection was usually initiated at 2:00 p.m.

One of the fertilized eggs was fixed and about 1–2 pl of DNA was microinjected into the male pronuclei by using the micropipette.

Example 4
Transplantation of the Injected Fertilized Egg into the Oviduct of Mouse The injected mouse eggs above were classified according to their states such as the healthy and the lysed. The lysed eggs were discarded and the intact eggs were cultured in mWM medium at 37° C. An anesthetic was injected into the abdominal cavity of receiver females and 20–25 of the injected fertilized eggs were reimplanted into the right oviduct. At that time, the receiver females which were affirmed for the presence of the vaginal plug after mating with the vasectomized males were utilized.

Example 5
DNA Separation from Mouse Tail Tissue

In order to analyze the injected DNA of the transgenic mice, DNA was extracted from approximately 1.5–2.0 cm of the tail end from over 3–4 week old offspring. The tail tissue was dissolved in 500 µl of tail-dissolving solution containing 100 mM Tris-HCl (pH8.5), 5mM EDTA (pH8.0), 200mM NaCl, 100 µg/ml proteinase K (Sigma, USA) and reacted at 55° C. for 10 hours. The reaction mixtures were voltexed for 20–30 sec. and rotated at 14,000 rpm for 5 min. to be sedimented. After centrifugation, chromosomal DNA was obtained by carrying out the extraction with phenol/chloroform/isoamylalcohol (25:24:1) and chloroform respectively, and by precipitating with 3M NaOAc/ethanol. The concentration of said chromosomal DNA was quantified by using spectrophotometer and adjusted to be 0.8 µg/µl.

Example 6
PCR Analysis

The H/K-ras gene of transgenic mice obtained as above was analyzed by using PCR which exploited oligonucleotides of SEQ ID. NO:3(ghras. pcr. for) and SEQ ID. NO:4(gras. pcr. rev) as a forward primer and a reverse primer respectively.

In details, 2 µg of the genomic DNA from the transgenic mice and 1 µl of each primer (0.27 µg/µl) above were added to the tube containing 10× reaction buffer 4 µl (Promega, USA), 25mM MgCl$_2$2.4 µg, 2mM dNTP 2.5 µl and Taq polymerase 1 unit (Promega, USA). The reaction mixture was adjusted to be 40 µl with D. W. and mineral oil was added to the supernatant of the reactions so as to prohibit the reactions from diffusion. PCR was performed at 74° C. for 70 sec 1 time and then repeated for 30 cycles (94° C. 60 sec, 55° C. 60 sec, 72° C. 60 sec) using the reaction mixture above. As a result, five clones have been proved to be transgenic mice carrying H/K-ras 4B gene by using polyacrylamide gel electrophoresis analysis (see FIG. 2).

Example 7
Southern Blot

In order to examine the injected gene by using Southern blot, probe DNA with radioactive marker was prepared. The expression vector pMAM neo genomic H-Ras-K-Ras 4B was added to the tube containing 10× reaction buffer 10 µl, restriction enzyme Nhe I , Xba I 2.5 µl respectively, and reacted at 37° C. for 2 hours. About 240bp fragment separated by using polyacrylamide gel electrophoresis and dissolved in 30 µl of D. W. (fragment 3).

2 µl of fragment 3 above was dissolved in 9 µl of D. W., denatured by heating for 10 min. at 100° C. and chilled in ice water. The solution above was added to High prime (Boeringer Mannheime, Germany) 4 µl, [α-$^{32}$P] dCTP (Amersham, England) 5 µl and reacted at 37° C. for 15 min. The said reaction mixtures were added to 80 µl D. W. and allowed to flow through Sephadex G-50 column (Pharmacia, USA) for removing monomers. The elute was boiled at 100° C. for 10 min. and chilled in ice water.

Chromosomal DNA (0.8 µg/µl) 12.5 µl was treated with 10× reaction buffer 10 µl and restriction enzyme Cla I, BamH I 3 µl respectively, adjusting total volume to 100 µl and reacted at 37° C. for 20 hours. The said reaction mixtures were added to ⅒ volumn of 3M NaOAc and twice volume of ethanol so as to precipitate chromosomal DNA.

Chromosomal DNA above was dissolved in 9 µl of D. W., and electrophoresed on 1% agarose gel (Biorad, USA) at 50V for 1 and a half hours. The gel was agitated for 30 min by using 0.4 M NaOH solution and washed with D. W. about 4 times.

After a support was placed inside a large dish filled with 10×SSC solution (0.15M sodium citrate/1.5M NaCl), Whatman 3M paper was laid on the top of the support. Upon the said paper the above agarose gel containing the genomic DNA was placed upside down. Positive charged nylon membrane, 2 pieces of Whatman 3M paper and paper towels were stacked in order and weighed down with 500g weight. Transfer of DNA was proceeded for 1/6 hours. The deposited nylon membrane was exposed to a source of UV irradiation so as to crosslink with DNA and allowed to stand at 80° C. for 2 hours.

A prehybridization solution was prepared by adding 100 µg/µl hering sperm DNA (Promega, USA) to the mixture of 2× prehybridization solution (5 prime→3 prime, USA)/formamide (1:1). The nylon membrane above was added to glass tube containing 10 µl of the said prehybridization solution, which was taken care to avoid producing air bubbles and reacted with Hybridizer (Techne, England) at 42° C. for 4 hours.

And then the prehybridization solution was replaced with the hybridization solution which was prepared by adding 100 µg/µl hering sperm DNA to the mixture of 2× prehybridization solution (5 prime→3 prime, USA)/formamide (1:1), probe DNA with radioactive marker was added and reacted with hybridizer at 42° C. for 16 hours.

The nylon membrane bounded with probe DNA was washed with 2×SSC/0.1% SDS for 5 min, washed again for 15 min with same solution, with 0.5×SSC/0.1% SDS, 0.1× SSC/0.1% SDS for 15 min respectively at room temperature. Finally, this membrane was washed with 0.1×SSC/1.0% SDS for 30 min at 42° C.

The wrapped nylon membrane was exposed to the screen of the Phoshoimager (Molecular dynamics, USA), allowed to stand for 4 hours and developed. As a result, five clones which were identified by performing PCR have been proved to carry H/K-ras 4B gene.

Transgenic mice of the present invention contain H/K-Ras 4B gene with valine of the 12th amino acid residue in their germ and somatic cells, and exhibit the pathology associated with mammary tumors over-expressing H/K-Ras 4B gene in mammary glands.

Since the amino acid sequence of the C-terminus originated from K-Ras 4B protein is an important element for farnesylation, transgenic mice above carrying H/K-ras 4B gene with mammary tumors can be used efficiently to evaluate the compounds inhibiting farnesyl transferase from fanesylating Ras proteins. Furthermore the said transgenic mice can be used fitly to examine oncogenic mechanism related with the abnormality of Ras signal transduction system and to evaluate the compounds spoiling said system.

What is claimed is:

1. A transgenic mouse having a mammary tumor whose genome comprises a mammalian H/K-ras 4B gene operably linked to a mouse mammary tumor virus (MMTV) promoter, wherein the H/K-ras 4B transgene is expressed in somatic cells and germ cells, and wherein said expression results in said mammary tumor.

2. The transgenic mouse according to claim 1, wherein the H/K-ras 4B gene comprises the N-terminal sequence of a H-ras 4B gene containing valine at the $12^{th}$ amino acid residue and the C-terminal sequence of a K-ras 4B gene.

3. The transgeneic mouse according to claim 1, wherein the H/K-ras 4B gene comprises 164 amino acids of the N terminal sequence of the H-ras 4B gene containing valine at the $12^{th}$ amino acid residue and 24 amino acids of the C-terminal sequence of the K-ras 4B gene.

4. An expression vector comprising pMAMneo comprising a H/K-ras 4B gene under the control of the mouse mammary tumor virus (MMTV) promoter.

5. The expression vector according to claim 4, wherein the H/K-ras 4B gene is inserted 3' to the MMTV promoter of the expression vector pMAM neo.

6. An E.coli transformant prepared by transforming E.coli MC1061 strain with the expression vector of claim 5, which is designated as E-coli MC1061/pMAM neo-genomic H-ras/K-ras 4B as deposited at the Korean Research Institute of BioScience and Biotechnology, Daeion, Korea, Dec. 2, 1997, accession number: KCTC 0411BP.

7. A method of making a transgenic mouse of claim 1, which comprises the steps of:

(a) cloning the first 164 amino acid residues of the H-ras gene comprising valine at the $12^{th}$ amino acid and the last 24 amino acids of the K-ras 4B gene, to form a H/K-ras 4B gene, wherein the H/K-ras 4 B gene is operably linked to the MMTV promoter;

(b) isolating the H/K-ras 4B gene for microinjection;

(c) microinjecting H/K-ras 4B gene into a fertilized mouse egg;

(d) transplanting the fertilized egg into a mouse oviduct;

(e) confirming the transfer of H/K-ras 4B gene into a mouse by PCR analysis and Southern blot; and (f) thereby producing said transgenic mouse.

* * * * *

SEQUENCE LISTING

<160> NUMBER OF SEQ ID NOS:    4

<210> SEQ ID NO 1
<211> LENGTH: 35
<212> TYPE: DNA
<213> ORGANISM: Artificial Sequence
<220> FEATURE:
<223> OTHER INFORMATION: oligonucleotide

<400> SEQUENCE: 1
gagccggcta ccatatgacg gaatataagc tggtg                              35

<210> SEQ ID NO 2
<211> LENGTH: 29
<212> TYPE: DNA
<213> ORGANISM: Artificial Sequence
<220> FEATURE:
<223> OTHER INFORMATION: oligonucleotide

<400> SEQUENCE: 2
gctgaggaat tccgtagctt cgggcgagt                                     29

<210> SEQ ID NO 3
<211> LENGTH: 24
<212> TYPE: DNA
<213> ORGANISM: Artificial Sequence
<220> FEATURE:
<223> OTHER INFORMATION: oligonucleotide

<400> SEQUENCE: 3
cccagggctt aagtaagttt ttgg                                          24

<210> SEQ ID NO 4
<211> LENGTH: 24

-continued

```
<212> TYPE: DNA
<213> ORGANISM: Artificial Sequence
<220> FEATURE:
<223> OTHER INFORMATION: oligonucleotide

<400> SEQUENCE: 4
cctgtactgg tggatgtcct caaa                                            24
```